(12) United States Patent
Papkovsky et al.

(10) Patent No.: US 9,188,536 B2
(45) Date of Patent: Nov. 17, 2015

(54) PHOTOLUMINESCENT PRESSURE PROBE

(75) Inventors: Dmitri Boris Papkovsky, Blarney (IE);
Richard Fernandes, Clane (IE)

(73) Assignee: LUXCEL BIOSCIENCES, LTD, Cork (IE)

( * ) Notice: Subject to any disclaimer, the term of this patent is extended or adjusted under 35 U.S.C. 154(b) by 525 days.

(21) Appl. No.: 13/521,253

(22) PCT Filed: Jan. 27, 2010

(86) PCT No.: PCT/EP2010/000498
§ 371 (c)(1),
(2), (4) Date: Jul. 10, 2012

(87) PCT Pub. No.: WO2011/091811
PCT Pub. Date: Aug. 4, 2011

(65) Prior Publication Data
US 2012/0295364 A1    Nov. 22, 2012

(51) Int. Cl.
| | | |
|---|---|---|
| G01N 31/22 | (2006.01) |
| G01N 21/64 | (2006.01) |
| G01L 1/24 | (2006.01) |
| G01L 11/02 | (2006.01) |
| G01M 3/22 | (2006.01) |
| G01M 3/38 | (2006.01) |

(52) U.S. Cl.
CPC .............. *G01N 21/6408* (2013.01); *G01L 1/24* (2013.01); *G01L 11/02* (2013.01); *G01M 3/226* (2013.01); *G01M 3/38* (2013.01); *Y10T 436/207497* (2015.01)

(58) Field of Classification Search
CPC ... G01N 33/525; G01N 31/22; G01N 33/521; G01N 33/54366; G01N 2021/6432; G01N 21/643; G01N 27/16; G01N 2021/7786; G01N 21/6428; G01N 21/75; B01L 3/502
USPC .......................................... 436/136; 422/401
See application file for complete search history.

(56) References Cited

U.S. PATENT DOCUMENTS

| | | | |
|---|---|---|---|
| 5,142,155 | A | 8/1992 | Mauze et al. |
| 5,407,829 | A * | 4/1995 | Wolfbeis et al. ................. 436/1 |
| 5,885,843 | A | 3/1999 | Ayers et al. |
| 6,330,464 | B1 | 12/2001 | Colvin, Jr. et al. |
| 6,468,222 | B1 | 10/2002 | Mault et al. |
| 7,569,395 | B2 | 8/2009 | Havens et al. |
| 8,093,055 | B2 | 1/2012 | Mayer et al. |
| 2004/0134821 | A1* | 7/2004 | Tornier ........................ 206/438 |
| 2007/0212461 | A1* | 9/2007 | Lillevang et al. ............ 426/320 |
| 2007/0212789 | A1* | 9/2007 | Havens et al. ................ 436/138 |
| 2007/0243618 | A1* | 10/2007 | Hatchett et al. .................. 436/1 |
| 2008/0161711 | A1 | 7/2008 | Orr et al. |
| 2009/0028756 | A1 | 1/2009 | Shahriari |
| 2010/0116017 | A1 | 5/2010 | Mayer et al. |

FOREIGN PATENT DOCUMENTS

| | | |
|---|---|---|
| EP | 0472243 A2 | 2/1992 |
| WO | 0133195 A1 | 5/2001 |
| WO | 2008055167 A2 | 5/2008 |

* cited by examiner

*Primary Examiner* — Lyle Alexander
*Assistant Examiner* — Dwan A Gerido
(74) *Attorney, Agent, or Firm* — Sherrill Law Offices, PLLC

(57) ABSTRACT

A self-contained, remotely interrogatable, autonomously positionable, pressure probe and methods of manufacturing and using. The probe (10) includes (i) a hermetically sealed, flexible, gas impermeable sachet (50) capable of equilibriating to a surrounding pressure, (ii) an optically-active, target-analyte partial pressure sensitive material (20) within the sachet, and (iii) a gaseous headspace (58) within the sachet containing a known concentration of the target-analyte (A).

23 Claims, 5 Drawing Sheets

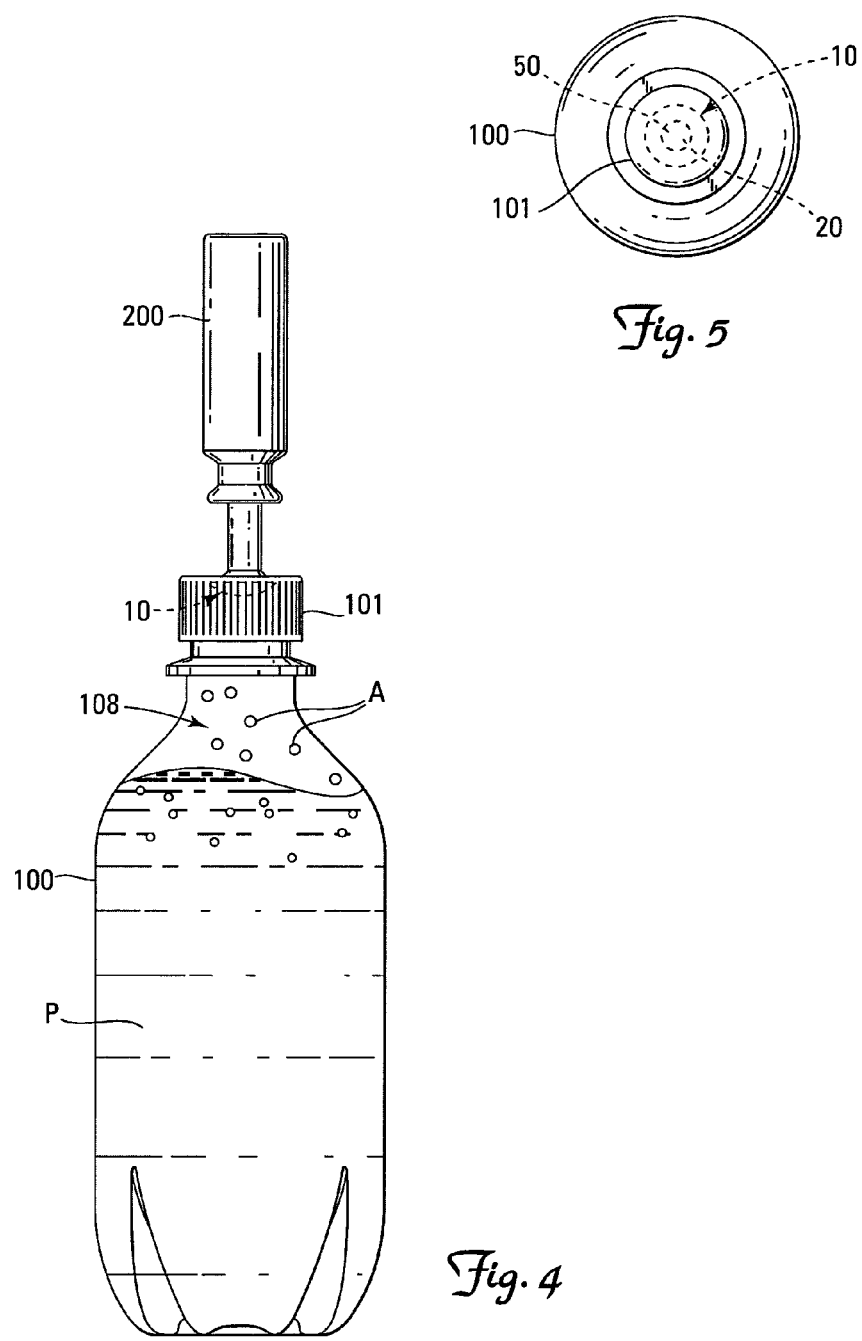

PHOTOLUMINESCENT PRESSURE PROBE

BACKGROUND

Solid-state polymeric materials based on oxygen-sensitive photoluminescent dyes are widely used as optical oxygen sensors and probes. See, for example United States Published Patent Applications 2009/0029402, 2008/8242870, 2008/215254, 2008/199360, 2008/190172, 2008/148817, 2008/146460, 2008/117418, 2008/0051646, and 2006/0002822, and U.S. Pat. Nos. 7,569,395, 7,534,615, 7,368,153, 7,138,270, 6,689,438, 5,718,842, 4,810,655, and 4,476,870. Such optical sensors are available from a number of suppliers, including Presens Precision Sensing, GmbH of Regensburg, Germany, Oxysense of Dallas, Tex., United States, and Luxcel Biosciences, Ltd of Cork, Ireland.

Such oxygen-sensitive photoluminescent dyes respond to the partial pressure of oxygen ($P_{O2}$), and are widely used in pressure-sensitive paints that can be applied to the surface of an object and interrogated to determine pressure distribution on the surface of the object. See, for example United States Published Patent Applications 2007/112166, 2007/105235, 2006/101906, 2005/288475, 2004/0249593, 2004/091695, and 2003/175511, and U.S. Pat. Nos. 7,290,444, 7,176,272, 7,127,950, 5,965,642, 5,854,682, 5,818,057, 5,612,492, 5,359,887, 5,341,676, 5,307,675, and 5,186,046.

Manufacturers and suppliers of labile products, such as medical and biological products, pharmaceuticals and foodstuffs, typically package such products in a hermetically sealed package that has been flushed with an inert gas, such as nitrogen, for purposes of reducing the concentration of oxygen within the package and thereby increasing the shelf-life of the product. It is known to employ oxygen sensitive optical probes within such packaging for providing a quick, easy, reliable and non-destructive means for measuring the concentration of oxygen within the packaging, from which the manufacturer can evaluate the integrity of the packaging process and/or the shelf-life status of packaged product in inventory. See, for example United States Published Patent Application 2009/0028756.

Manufacturers and suppliers of such labile products also often desire to measure the pressure within the package instead of or in addition to measuring the concentration of oxygen, again for purposes of evaluating the integrity of the packaging process and/or evaluating the remaining shelf-life of packaged product in inventory (e.g., an increase in pressure within a bag of potato chips is indicative of deterioration of the chips and resultant loss of taste and shelf-life while a decrease in pressure within a bottle of a carbonated beverage is indicative of a loss of carbonation and resultant loss of taste and shelf-life). Unfortunately, the current methods available to manufacturers and suppliers for measuring pressure within a hermetically sealed package are prohibitively slow and cumbersome or destructive of the package being tested.

Hence, a substantial need exists for a quick, easy, reliable and non-destructive means for measuring the pressure within hermetically sealed packaging.

SUMMARY OF THE INVENTION

A first aspect of the invention is an article of commerce comprising a self-contained, remotely interrogatable, autonomously positionable, pressure probe. The pressure probe includes at least (i) a hermetically sealed, flexible, gas impermeable sachet capable of dynamically equilibriating to a surrounding pressure, (ii) an optically-active, target-analyte partial pressure sensitive material within the sachet, and (iii) a gaseous headspace within the sachet containing a known concentration of the target-analyte. The target-analyte partial pressure sensitive material is preferably a solid state composition of an oxygen partial-pressure sensitive photoluminescent dye embedded within an oxygen-permeable polymer matrix.

The sachet is preferably made of a material with a very low gas permeability, most preferably a material that is gas impermeable, so as to prevent any meaningful change in the composition of the gas within the headspace of the sachet over the intended lifespan of the probe.

A second aspect of the invention is an article of commerce comprising a hermetically sealed package containing (i) a product, (ii) a gaseous headspace within the package, and (iii) a pressure probe according to the first aspect of the invention within the package.

The pressure probe can be in fluid communication with the product or the gaseous headspace.

A third aspect of the invention is a method for determining the pressure within a hermetically sealed package employing a pressure probe according to the first aspect of the invention. The method includes the steps of (A) obtaining a hermetically sealed package according to the second aspect of the invention, (B) allowing the pressure within the sachet to equilibriate to the pressure within the package, (C) obtaining an analytical instrument capable of reading the optical activity of the pressure probe, (D) taking a reading from the probe with the analytical instrument, (E) correlating the value of the reading to a total pressure value within the sachet employing Dalton's Law of Partial Pressure, and (F) reporting the total pressure value as the pressure within the package.

A fourth aspect of the invention is a method of manufacturing a pressure probe according to the first aspect of the invention. The method includes the steps of (A) preparing a coating cocktail which contains an oxygen partial pressure sensitive photoluminescent dye and a suitable carrier matrix in an organic solvent, (B) applying the cocktail to a support material, (C) allowing the applied cocktail to dry, whereby a solid-state thin film coating of an optically active oxygen partial pressure sensitive material is formed on the support to create a sensor, and (D) hermetically sealing the sensor and a gas having a known concentration of oxygen within a flexible, gas impermeable sachet so as to form a self-contained, remotely interrogatable, autonomously positionable, pressure probe capable of equilibriating to a surrounding pressure.

BRIEF DESCRIPTION OF THE DRAWINGS

FIG. 4 is a side view of one embodiment of a hermetically sealed bottle containing a carbonated beverage and a pressure probe as depicted in FIG. 1 with the pressure probe being interrogated by an analytical instrument.

FIG. 5 is top view of the bottle depicted in FIG. 3.

DETAILED DESCRIPTION OF A PREFERRED EMBODIMENT

Definitions

Figure 1:
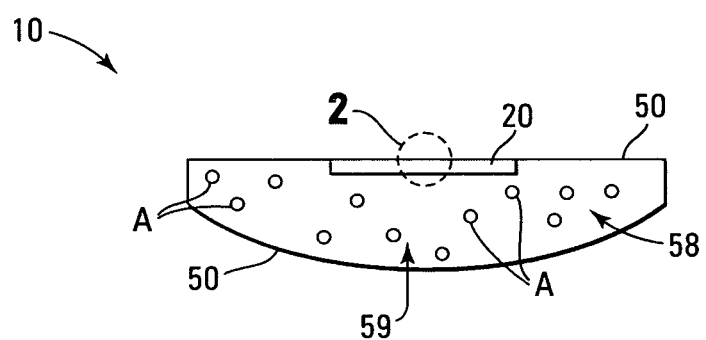
FIG. 1 is an enlarged side-view of one embodiment of the pressure probe aspect of this invention.

As used herein, including the claims, the phrase "gas impermeable" means a gas transmission rate of less than 30 $c^3/m^2$ day when measured in accordance with ASTM D1434.

As used herein, including the claims, the term "target-analyte" refers to a gaseous chemical substance, typically $O_2$, or $CO_2$, capable of quenching an optically-active material such as a photoluminescent dye.

Nomenclature

10 Probe
20 Solid State Composition
21 Target-Analyte-Sensitive Photoluminescent Dye
22 Target-Analyte-Permeable Polymer Matrix
30 Support Layer
30a First or Upper Major Surface of Support Layer
30b Second or Lower Major Surface of Support Layer
40 Pressure Sensitive Adhesive Layer
50 Sachet
58 Headspace within Sachet
59 Cavity Defined by Sachet
100 Packaging or Container
101 Transparent or Translucent Cap or Covering on Package
108 Headspace within the Packaging
200 Analytical Instrument
A Target-Analyte
P Product Description Theory The methods and compositions described herein are based on the quenching of photoluminescence by a target-analyte, typically oxygen ($O_2$). Luminescence encompasses both fluorescence and phosphorescence. Electromagnetic radiation in the ultraviolet or visible region is used to excite molecules to higher electronic energy levels. The excited molecules lose their excess energy by one of several methods. One of those methods is fluorescence. Fluorescence refers to the radiative transition of electrons from the first excited singlet state to the singlet ground state ($S_1$ to $S_0$). The lifetime of fluorescence is relatively short, approximately $10^{-9}$ to $10^{-7}$ seconds. However, intersystem crossing from the lowest excited singlet state to the triplet state often occurs and is attributed to the crossing of the potential energy curves of the two states. The triplet state so produced may return to the ground state by a radiative process known as phosphorescence. Phosphorescence is the radiative relaxation of an electron from the lowest excited triplet state to the singlet ground state ($T_1$ to $S_0$). Because the transition that leads to phosphorescence involves a change in spin multiplicity, it has a low probability and hence a relatively long lifetime of $10^{-4}$ to 10 seconds. Fluorescent and phosphorescent lifetime is known to change in a defined fashion relative to changes in the partial pressure of a target-analyte capable of quenching the photoluminescent molecules. Hence, the partial pressure of a target-analyte in fluid communication with a photoluminescent material can be determined by measuring photoluminescence lifetime.

The present invention utilizes the sensitivity of photoluminescent dyes to the partial pressure of target-analytes and Dalton's Law of Partial Pressure to provide a probe capable of noninvasively measuring pressure.

Dalton's Law of Partial Pressure establishes that the total pressure ($P_{Total}$) of an ideal gaseous mixture is equal to the sum of the partial pressures of the individual constituent gases ($P_n$). This law is represented mathematically for a two constituent mixture as:

$$\text{Pressure}_{Total} = \text{Pressure}_1 + \text{Pressure}_2$$

A corollary to Dalton's Law of Partial Pressure establishes that a percentage change in the total pressure of a compositionally static gaseous mixture results in an identical percentage change in the partial pressure of each constituent gas. This corollary law is represented mathematically for a two constituent mixture as:

$$(\Delta P_{Total})/(P_{Total\ Start}) = (\Delta P_1)/(P_{1\ Start}) = (\Delta P_2)/(P_{2\ Start})$$

Wherein $\Delta P = P_{New} - P_{start}$

Application of these laws permits the total pressure (Pressure$_{Total}$) of a compositionally static gaseous mixture to be calculated from a determination of the partial pressure of a given constituent of that gaseous mixture (Pressure$_1$) so long as at least one pair of correlated values for total pressure (Pressure$_{Total}$) and partial pressure (Pressure$_1$) of that constituent gas are known. For example, a gaseous mixture of 79% $N_2$ and 21% $O_2$ (i.e., air) at a total pressure ($P_{Air}$) of 1 atmosphere (101.325 kPa) is known to have a nitrogen partial pressure $P_{N2}$ of 0.79 atmospheres (80.047 kPa) and an oxygen partial pressure $P_{O2}$ of 0.21 atmospheres (21.278 kPa). If a subsequent analysis of this gaseous mixture indicates that the $P_{O2}$ has increased from 21.278 kPa to 30.000 kPa, the total pressure of the air ($P_{Air}$), assuming no change in the composition of the air, can be calculated as follows:

$$\Delta P_{O2} = 30.000\ \text{kPa} - 21.278\ \text{kPa} = 8.722\ \text{kPa}$$

$$(\Delta P_{O2})/(P_{O2\ Start}) = 8.722\ \text{kPa}/21.278\ \text{kPa} = 0.410$$

$$(\Delta P_{Total})/(P_{Total\ Start}) = 0.410$$

$$(P_{Total\ New} - P_{Total\ Start})/(P_{Total\ Start}) = 0.410$$

$$(P_{Total\ New} - 101.325\ \text{kPa})/(101.325\ \text{kPa}) = 0.410$$

$$P_{Total\ New} = 142.868\ \text{kPa}$$

A first aspect of the invention is a probe 10 capable of reporting the partial pressure of a target-analyte A ($P_A$) having a known concentration in a compositionally static gaseous mixture. Such information permits the total pressure of the gaseous mixture ($P_{Total}$) to be calculated as described above. The probe 10 is constructed so that $P_{Total}$ of the compositionally static gaseous mixture will dynamically equilibrate to the surrounding pressure, thereby ensuring that the calculated total pressure of the gaseous mixture equals the total pressure of the surrounding environment, such as the headspace of a filled beverage bottle or the headspace of a filled retort package. The probe 10 is inexpensive, self-contained, remotely interrogatable and autonomously positionable, thereby permitting the probe 10 to used for a wide variety of purposes to quickly, easily and reliably measure and monitor pressure within a sealed chamber in a non-invasive and non-destructive manner.

Construction

Figure 2:
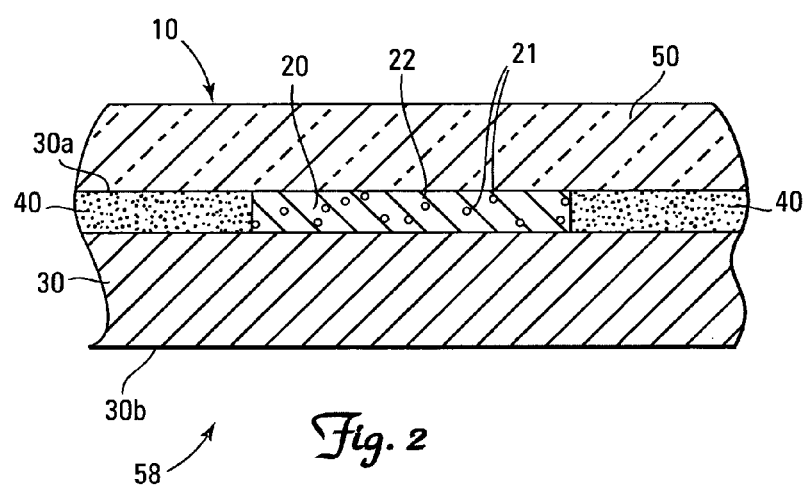
FIG. 2 is a grossly enlarged cross-sectional side view of a central portion of the pressure probe depicted in FIG. 1.
Figure 3:
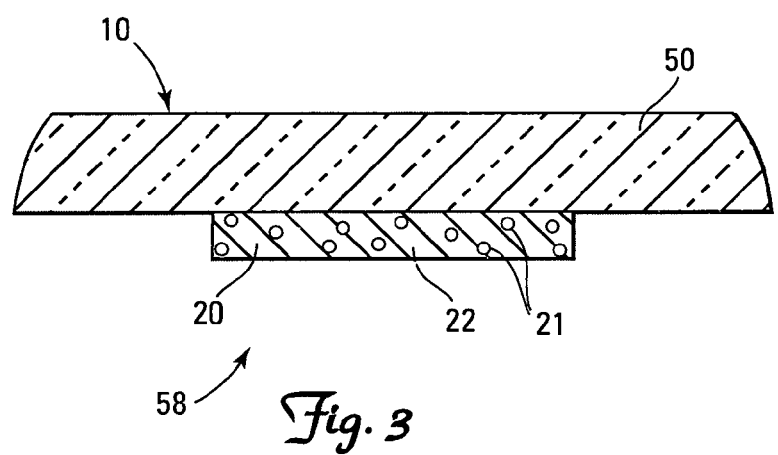
FIG. 3 is a grossly enlarged cross-sectional side view of a central portion of a second embodiment of the pressure probe aspect of this invention.

Referring generally to FIGS. 1, 2 and 3, a first aspect of the invention is a target-analyte partial pressure sensitive pressure probe 10 useful for optically ascertaining the pressure within an enclosed space, such as the retention chamber of a hermetically sealed package 100. The probe 10 is comprised of a hermetically sealed, flexible, gas impermeable sachet 50 with a thin film of a solid state photoluminescent composition 20 that is sensitive to the partial pressure of a target-analyte A retained within the sachet 50 within along with a gaseous headspace 58 containing a known concentration of the target-analyte A.

The sachet 50 defines an enclosed cavity 59 that contains a photoluminescent composition 20 sensitive to the partial pressure of a target analyte A, and a gaseous headspace 58 containing a known concentration of the target-analyte A. The cavity 59 is hermetically sealed and the sachet 50 constructed from a gas impermeable material for purposes of ensuring that the composition of the gas within cavity 59 does not appreciably change during the intended lifespan of the probe 10. A change in the composition of the gas within the cavity 59 can introduce significant error as both the sensor readings and the subsequent calculations utilizing those sensor readings are based upon the assumption that any change in target-analyte partial pressure results exclusively from a change in pressure, not a change in the concentration of target-analyte. The sachet 50 is also sufficiently flexible to ensure that the pressure within the cavity 59 dynamically equilibrates to the surrounding pressure, thereby allowing the pressure of the gas within the cavity 59 ascertained by interrogating the probe 10 to be equated to the pressure surrounding the probe 10. Those of routine skill in the art are capable of selecting suitable materials for use in constructing the sachet 50. A nonexhaustive list of suitable materials from which the sachet 50 may be constructed includes specifically, but not exclusively, polymeric films made of polyester (e.g., Mylar®), polyvinylidene chloride (PVDC), polyethylene vinyl alcohol (EVOH) and laminates based on these polymers, and other films which possess or have been coated to provide very low gas permeability characteristics.

The gaseous headspace 58 within the sachet 50 contains a known concentration of a target-analyte A. The amount of target-analyte A within the headspace 58 need not be strictly controlled, but must be known, needs to remain substantially constant throughout the lifespan of the probe 10, and should fall within a concentration that provides good sensitivity over the anticipated changes in target-analyte partial pressure. For example, when the target-analyte A is oxygen ($O_2$) it is convenient to simply fill the headspace 58 with air which contains 21% $O_2$ by volume. However, the sensitivity of the probe 10 within higher pressure ranges can be enhanced by limiting the $O_2$ concentration within the headspace to a concentration of between 0.2 to 20% by volume $O_2$, preferably 2 to 10% by volume $O_2$, and most preferably between 3 to 6% by volume $O_2$. Concentrations below 0.2% tend to lose sensitivity due to an overly diminished quenching of the photoluminescent dye 21 while concentrations above 21% tend to lose sensitivity as changes in quenching of the photoluminescent dye 21 resulting from changes in $P_{O2}$ are overwhelmed by the total quenching effect of the $O_2$ to which the photoluminescent dye 21 is exposed.

The solid state photoluminescent composition 20 may either be coated onto a support layer 30 as depicted in FIG. 2, or coated directly onto the interior surface of the sachet 50 as shown in FIG. 3.

For purposes of simplicity only, and without intending to be limited thereto, the balance of the description shall reference $O_2$ as the target-analyte A since $O_2$-sensitive probes are the most commonly used types of optically active probes.

The solid state photoluminescent composition 20 includes an oxygen partial pressure sensitive ($P_{O2}$ sensitive) photoluminescent dye 21 embedded within an oxygen-permeable polymer matrix 22.

The oxygen-sensitive photoluminescent dye 21 used in the solid state photoluminescent composition 20 may be selected from any of the well-known $P_{O2}$ sensitive photoluminescent dyes 21. One of routine skill in the art is capable of selecting a suitable dye 21 based upon the intended use of the probe 10. Preferred photoluminescent dyes 21 are long-decay fluorescent or phosphorescent dyes. A nonexhaustive list of suitable $P_{O2}$ sensitive photoluminescent dyes 21 includes specifically, but not exclusively, ruthenium(II)-bipyridyl and ruthenium (II)-diphenylphenanothroline complexes, porphyrin-ketones such as platinum(II)-octaethylporphine-ketone, platinum (II)-porphyrin such as platinum(II)-tetrakis(pentafluorophenyl)porphine, palladium(II)-porphyrin such as palladium(II)-tetrakis(pentafluorophenyl)porphine, phosphorescent metallocomplexes of tetrabenzoporphyrins, chlorins, azaporphyrins, and long-decay luminescent complexes of iridium (III) or osmium(II).

Typically, the hydrophobic $P_{O2}$-sensitive photoluminescent dye 21 is compounded with a suitable oxygen-permeable and hydrophobic carrier matrix 22. Again, one of routine skill in the art is capable of selecting a suitable oxygen-permeable hydrophobic carrier matris 22 based upon the intended use of the probe 10 and the selected dye 21. A nonexhaustive list of suitable polymers for use as the oxygen-permeable hydrophobic carrier matris 22 includes specifically, but not exclusively, polystryrene, polycarbonate, polysulfone, polyvinyl chloride and some co-polymers.

Referring to FIG. 2, when the solid state photoluminescent composition 20 is coated onto a support layer 30 the probe 10 preferably includes a layer of a pressure sensitive adhesive 40 on a major surface of the support layer 30 for facilitating attachment of the probe 10 to the interior surface of the sachet 50 with the photoluminescent solid state composition 20 facing outward through an area of the sachet 50 that is transparent or translucent to radiation at the excitation and emission wavelengths of the dye 21 in the photoluminescent solid state composition 20. The adhesive 40 may but should not cover the photoluminescent solid state composition 20.

Similarly, the probe 10 can include a layer of a pressure sensitive adhesive (not shown) on at least a portion of the exterior surface of the sachet 50 for facilitating attachment of the probe 10 to the interior surface of a container 100 that defines the enclosed space whose $P_{O2}$ is to be measured with the photoluminescent solid state composition 20 on the probe 10 facing outward from the container 100 through an area of the container 100 that is transparent or translucent to radiation at the excitation and emission wavelengths of the dye 21 in the photoluminescent solid state composition 20.

The support layer 30 may be selected from any of the materials commonly employed as a support layer for a $P_{O2}$ sensitive photoluminescent solid state composition 20. One of routine skill in the art is capable of selecting the material based upon the intended use of the probe 10. A nonexhaustive list of substrates includes specifically, but not exclusively, cardboard, paperboard, polyester Mylar® film, non-woven spinlaid fibrous polyolefin fabrics, such as a spunbond polypropylene fabric. When the solid state photoluminescent composition 20 is coated directly onto the interior surface of the sachet 50, the material used to construct the sachet 50 needs to be selected to provide both those properties and characteristics necessary to function as the sachet 50 as well as those properties and characteristics necessary to function as a support layer 30. One such example is Mylar® film.

The support layer 30 is preferably between about 30 μm and 500 μm thick.

The materials of construction can be selected to provide the probe 10 with an appropriate balancing of cost and useful lifespan. Generally, the probe 10 should be constructed to ensure a useful lifespan of at least two to three months, preferably six to twelve months, for purposes of allowing the probe 10 to be retained in inventory for several months prior to use and providing a probe 10 that can remain effective from a few weeks to a few months after it has been deployed in a hermetically sealed package or container 100.

Figure 6:
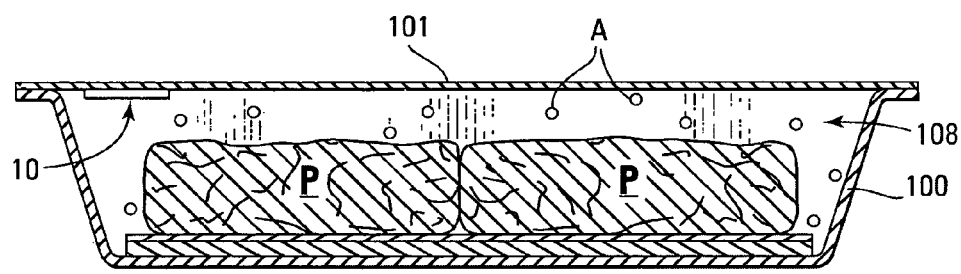
FIG. 6 is a side view of one embodiment of a hermetically sealed container containing a labile food product and a pressure probe as depicted in FIG. 1.

Referring generally to FIGS. 4, 5 and 6, a second aspect of the invention is an article of commerce comprising a product P, typically a labile product P, packaged within a hermetically sealed container 100 with a pressure probe 20 positioned within the headspace 108 of the container 100.

The probe 20 should be positioned within the headspace 108 of the container 100 so that the probe 20 can be easily located and the $P_{O2}$ sensitive photoluminescent solid state composition 20 presented for interrogation by an analytical reader (i.e. a light detector) 200 through the packaging 100 and through the sachet 50. As with the sachet 50, at least that portion of the packaging 100 overlaying the probe 20 needs to be transparent or translucent to radiation at the excitation and emission wavelengths of the dye 21 in the photoluminescent solid state composition 20 retained within the probe 10 so that the probe may be interrogated by an analytical reader 200 in a noninvasive and nondestructive manner.

It is noted that the concentration of target-analyte A within the headspace 108 of the container 100 does not impact readings taken from the probe 10 as the photoluminescent solid state composition 20 is never exposed to the gaseous content of the packaging 100. Hence, the probe 10 is capable of providing accurate measurements of pressure within the container 100 regardless of the complete absence or change in concentration within the headspace 108 of the container.

The ability to quickly and inexpensively monitor the pressure within a sealed container 100 in a nondestructive and noninvasive manner is particularly valuable when the product P within the container 100 is a labile product P that is subject to either (i) gas generative deterioration or spoilage, as is true for a wide variety of foodstuffs such as processed cereals, snack foods, prepared meals and meats, or (ii) deterioration due to a loss pressure, such as that observed with carbonated beverages.

It is also valuable in situations where the product P has been packaged under vacuum and a premature loss of vacuum can significantly affect the shelf-life of the product P, such as tuna vacuum packed in a gusseted pouch.

Still further, it is valuable in situations where pressure within the packaging is expected to increase or decrease shortly after the product P has been packaged within the container 100, such as is observed when foodstuffs are sealed within the packaging 100 while still hot, and thereafter cooled to room temperature or below.

Manufacture

The $P_{O2}$-sensitive solid state composition component 20 of the probe 10 can be manufactured by the traditional methods employed for manufacturing such probes 10. Briefly, the component 20 can be conveniently manufactured by (A) preparing a coating cocktail (not shown) which contains the photoluminescent $P_{O2}$-sensitive dye 21 and the oxygen-permeable polymer 22 in an organic solvent (not shown) such as ethylacetate, (B) applying the cocktail to the first major surface 30a of a support material 30 or soaking the support material in the cocktail (not shown), and (C) allowing the cocktail (not shown) to dry, whereby a solid-state thin film coating 20 is formed on the support 30. The resultant $P_{O2}$-sensitive solid state composition component 20 is preferably heat treated to remove mechanical stress from the sensor material which is associated with its preparation (solidification and substantial volume reduction).

Generally, the concentration of the polymer 22 in the organic solvent (not shown) should be in the range of 0.1 to 20% w/w, with the ratio of dye 21 to polymer 22 in the range of 1:50 to 1:5,000 w/w.

A layer of pressure sensitive adhesive 40 can optionally be coated onto the first major surface 30a of the support material 30 by conventional coating techniques.

The probe 10 can then be assembled by placing the $P_{O2}$-sensitive solid state composition component 20 between upper and lower layers of a flexible, gas impermeable film, such as Mylar, and forming a hermetically sealed sachet 50 from the upper and lower layers of film that encloses component 20 and provides a supply of a gas, such as air, with the headspace 58 of the sachet 50 having a known concentration of oxygen.

One of routine skill in the art would also be able to produce a supply of the probes 10 in the form of an array, such as by incorporating a $P_{O2}$-sensitive solid state composition component 20 within each "bubble" in a blister pack array or sheet of bubble wrap.

Use

The probe 10 can be used to quickly, easily, accurately and reliably measure the pressure within a hermetically sealed package 100. The probe 10 can be interrogated and used to measure pressure in essentially the same manner as a typical oxygen sensitive photoluminescent probe is interrogated and used to measure the concentration of a target-analyte A within an enclosed space. Briefly, the probe 10 is used to measure pressure within a hermetically sealed package 100 by (A) placing the probe 10 within the cavity of the package 100 at a location that is in fluid communication with the gaseous headspace 108 in the cavity and where radiation at the excitation and emission wavelengths of the dye 21 can be transmitted to and received from the photoluminescent solid state composition 20 with minimal interference and without opening or otherwise breaching the integrity of the package 100, such as a transparent or translucent cap 101 on a bottle 100 or covering 101 on a container 100, (B) allowing the pressure within the sachet 50 to equilibriate to the pressure within the package 100—typically less than several seconds, (C) ascertaining the total pressure within the sachet 50 by (i) repeatedly exposing the probe 10 to excitation radiation over time, (ii) measuring radiation emitted by the excited probe 10 after at least some of the exposures, (iii) measuring passage of time during the repeated excitation exposures and emission measurements, (iv) converting at least some of the measured emissions to a target-analyte A partial pressure ($P_A$) within the sachet 50 based upon a known conversion algorithm or look-up table, and (v) calculating the total pressure within the sachet 50 from the determined target-analyte A partial pressure ($P_A$) within the sachet 50 by applying Dalton's Law of Partial Pressure and its corallary and at least one known pair of correlated values for total pressure ($Pressure_{Total}$) and partial pressure of the target-analyte A ($P_A$), and (D) equating the calculated total pressure within the sachet 50 to the pressure within the packaging 100. The conversion algorithms employed in this process are well know to and readily developable by those with routine skill in the art.

Interrogation of the probe 10 to ascertain the total pressure within the sachet 50 is accomplished in a non-destructive fashion with an external detector 200.

The probes 10 may be sensitive to temperature. In order to ensure accurate pressure measurements readings obtained from the probe 10 may need to be adjusted to compensate for any temperature induced variation. These relationships are well known and widely published for oxygen sensitive photoluminescent solid state compositions 20.

For particular applications, the probe 10 may be used to signal "expiration" of a packaged labile product P by programming the analytical instrument 200 used to interrogate a probe 10 within a package 100 to compare the pressure within the package 100 determined by interrogating the probe 10 to a predetermined threshold value indicative of product P expiration, and generate a signal when the measured pressure value falls beyond that threshold value, indicating that the product P should not be sold for human consumption.

The radiation emitted by the excited probe 10 can be measured in terms of intensity and/or lifetime (rate of decay, phase shift or anisotropy), with measurement of lifetime generally preferred as a more accurate and reliable measurement technique when seeking to establish oxygen partial pressure via measurement of the extent to which the dye 21 has been quenched by oxygen.

EXAMPLES

Example 1

Manufacture of Pressure Sensor Inserts

One milligram of the phosphorescent oxygen-sensitive dye PtOEPK (platinum(II) octaethylporphyrinketone) was dissolved in 4 ml of 2.5% solution of polystyrene (M.W. 280,000) in ethylacetate to form a cocktail. This cocktail was applied with a micropipette in 5 µL aliquots on a 155 µm thick microporous polypropylene membrane and allowed to dry, forming an array of solid-state $O_2$ sensors. Individual sensors were produced by cutting the membrane in dots having a diameter of approximately 10 mm.

The sensors were batch-calibrated using a set of standards (0-100% $O_2$ gas balanced with $N_2$) and a Luxcel fibre-optic detector to obtain phosphorescence phase shift readings. These readings were performed at ambient pressure and temperature (25° C.).

Example 2

Manufacture of Air Filled Pressure Probes

Sachets were formed from a film laminate of PET/PVDC/PP. Each sachet was formed by overlapping two 8×8 cm pieces of the film and heat-sealing the layers together along three sides with a double seal employing an industrial heat-sealing machine—forming a pouch with an open end. One of the $O_2$ sensor inserts formed in Example 1 was inserted inside the pouch through the open end and positioned within the pouch so that the $O_2$ sensor faced the wide side and could be interrogated from outside the pouch. A styrofoam insert was placed within the pouch through the open end to ensure that the pouch retained a volume of air when sealed. The open end of the pouch was then sealed under ambient air pressure and excess film removed with a pair of scissors to form pressure probes, each comprising a hermetically sealed sachet with an $O_2$ sensor and a supply of air retained within an approximately 3×3 cm cavity.

Example 3

Manufacture of Reduced Oxygen Filled Pressure Probes

Probes were formed in accordance with Example 2 except that the pouches were flushed with a gas containing approximately 5% oxygen just prior to sealing the open end of the pouch. One of these probes was monitored ambient temperature and pressure in room air using a phosphorescent phase detector over a 24 hour period. During this period no significant changes in sensor phase signal were observed, indicating that the sachet material and fabrication technology provide an effective gas-barrier.

Example 4

Manufacture of Air Filled Pressure Probes

One milligram of the phosphorescent oxygen-sensitive dye PtOEPK (platinum(II) octaethylporphyrinketone) was dissolved in 4 ml of 2.5% solution of polystyrene (M.W. 280,000) in ethylacetate to form a cocktail. This cocktail was applied with a micropipette in 5 µL aliquots onto a film laminate of PET/PVDC/PP and allowed to dry, forming an array of solid-state $O_2$ sensors.

Sachets were formed from the film laminate of PET/PVDC/PP upon which the $O_2$ sensors were formed, each containing a single $O_2$ sensor on the inside surface of the sachet. Square 8×8 cm pieces of the film were cut out and folded so as to position the $O_2$ sensor between the folded layers of film. A styrofoam insert was placed between the folded layers of film to ensure that the sachet retained a volume of air when sealed, and the folded layers heat-sealed tightly with a double seal along all three sides. Excess film was removed with a pair of scissors to form pressure probes, each comprising a hermetically sealed sachet with an $O_2$ sensor and a supply of air retained within an approximately 3×3 cm cavity.

Example 5

Use of Air Filled Pressure Probe to Measure Air Induced Pressure Changes

One of the pressure probes manufactured in Example 2 was inserted into and attached to the inner wall of a 100 ml bottle. A Luxcel fiber-optic phosphorescence phase detector was positioned to interrogate the probe through the wall of the bottle.

The bottle was sealed with an air-tight cap having an inlet and an outlet flow channel therethrough. The inlet flow channel was connected to a cylinder of compressed air. The outlet channel was closed and the internal pressure inside the bottle increased gradually by means of a pressure regulator on the cylinder of compressed air. Phase/lifetime signals were obtained from the probe by the detector at ambient pressure and at stepwise increases in pressure of 1.0 and 2.0 Bar above ambient pressure. Results are reported in Table One below. As shown in Table One, a stepwise change in phase signal was observed at each stepwise change in pressure. Such changes were in agreement with the $P_{O2}$ calibration of the probe.

TABLE ONE

| PRESSURE INSIDE BOTTLE | PHASE SIGNAL (DEGREES) |
| --- | --- |
| Ambient | 11.1 |
| Ambient + 1.0 Bar | 7.2 |
| Ambient + 2.0 Bar | 3.7 |

Upon the release of pressure within the bottle, the phase/lifetime signal obtained from the probe quickly returned to its original value, indicating that the probe responds quickly and reversibly to changes in external pressure with a corresponding change in phosphorescence intensity and decay characteristics.

The probe was then exposed to a reduced pressure of 0.8 Bar with a concomitant increase in sensor signal (phase shift).

Example 6

Use of Air Filled Pressure Probe to Measure Carbon Dioxide Induced Pressure Changes Example 5 was duplicated, except that the inlet flow channel was connected to a cylinder of compressed carbon dioxide. The probe produced practically the same changes in its phosphorescent signal as when air was used to change the pressure within the bottle. This illustrates that the probes response to changes in surrounding pressure is consistent and independent from the composition of the external gas applying pressure upon the probe.

Example 7

Use of Reduced Oxygen Pressure Probe to Measure Air Induced Pressure Changes

Example 5 was duplicated, except that a pressure probe of Example 3 was employed. Phase/lifetime signals were obtained from the probe by the detector at ambient pressure and at stepwise increases in pressure of 0.5, 1.0, 1.5 and 2.0 Bar above ambient pressure. Results are reported in Table Two below. As shown in Table Two, a stepwise change in phase signal was observed at each stepwise change in pressure. Such changes were in agreement with the $P_{O2}$ calibration of the probe. The probe produced a distinct and reversible response to changes in external pressure, but with a larger signal change in response to smaller changes in external pressure from ambient pressure relative to the pressure probe of Example 2.

TABLE TWO

| PRESSURE INSIDE BOTTLE | PHASE SIGNAL (DEGREES) |
|---|---|
| Ambient | 21.44 |
| Ambient + 0.5 Bar | 18.77 |
| Ambient + 1.0 Bar | 16.29 |
| Ambient + 1.5 Bar | 13.61 |
| Ambient + 2.0 Bar | 11.17 |

Example 8

Use of Air Pressure Probe to Measure Air Induced Pressure Changes

Example 5 was duplicated, except that a pressure probe of Example 4 was employed. The probe produced a distinct and reversible response to changes in external pressure consistent with the responses observed in Examples 5 and 6.

We claim:

1. An article of commerce, comprising a hermetically sealed package containing (a) a product, (b) a package gaseous headspace within the package, and (c) a self-contained, remotely interrogatable, autonomously positionable, pressure probe within the package, the probe comprising at least (i) a hermetically sealed, flexible, gas impermeable sachet having a sachet gaseous headspace containing a known non-zero concentration of target-analyte capable of equilibriating to a surrounding pressure, and (ii) an optically-active, target-analyte partial pressure sensitive material within the sachet headspace.

2. The article of claim 1 wherein the headspace is filled with air.

3. The article of claim 1 wherein the optically active material is a photoluminescent material sensitive to the partial pressure of oxygen.

4. The article of claim 1 wherein the product is subject to gas generative deterioration or spoilage.

5. The article of claim 1 wherein the product is subject to gas consuming deterioration or spoilage.

6. The article of claim 1 wherein a pressure increase within the packaging after the packaging is sealed is desired and expected.

7. The article of claim 1 wherein a pressure decrease within the packaging after the packaging is sealed is desired and expected.

8. The article of claim 1 wherein the optically active material can be optically interrogated through both the sachet and the packaging.

9. The article of claim 1 wherein the optically active material is sensitive to the partial pressure of oxygen.

10. The article of claim 9 wherein the sachet headspace is filled with air.

11. The article of claim 9 wherein the sachet headspace is filled with a gas containing between 3 and 6% oxygen.

12. The article of claim 1 wherein the optically active material is sensitive to the partial pressure of carbon dioxide.

13. The article of claim 12 wherein the sachet is constructed of a carbon dioxide impermeable film.

14. The article of claim 13 wherein the sachet headspace is filled with air.

15. A method of determining the pressure within a hermetically sealed package, comprising the steps of:
(a) obtaining a hermetically sealed package according to claim 1,
(b) allowing the pressure within the sachet to equilibriate to the pressure within the package,
(c) obtaining an analytical instrument capable of reading the optical activity of the pressure probe,
(d) taking a reading from the probe with the analytical instrument,
(e) correlating the value of the reading to a total pressure value within the sachet, and
(f) reporting the total pressure value as the pressure within the packaging.

16. The method of claim 15 wherein readings and correlations are based upon photoluminescence lifetime of the probe.

17. The method of claim 15 further comprising the steps of comparing the total pressure value to a predetermined threshold value and signaling when the total pressure value exceeds the threshold value, indicating that the product should not be sold for human consumption.

18. The method of claim 15 further comprising the steps of comparing the total pressure value to a predetermined threshold value and signaling when the total pressure value is less than the threshold value, indicating that the product should not be sold for human consumption.

19. The method of claim 15 wherein the optically active material is optically interrogated by the analytical instrument in a contactless nondestructive manner through the sachet and the package.

20. The method of claim 15 wherein the pressure probe contained within the hermetically sealed package has been calibrated with at least one known pressure value at the known concentration of the target-analyte before the package is obtained.

21. The method of claim 20 wherein the at least one known pressure value is ambient pressure.

22. The method of claim 15 wherein the optically active material is sensitive to the partial pressure of oxygen.

23. The method of claim 22 wherein the sachet headspace is filled with air.

* * * * *